United States Patent
Steiger et al.

(10) Patent No.: US 7,838,737 B1
(45) Date of Patent: Nov. 23, 2010

(54) SOYBEAN VARIETY XB39N09

(75) Inventors: Debra K. Steiger, Wauseon, OH (US); Paul A. Stephens, Princeton, IL (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 12/424,585

(22) Filed: Apr. 16, 2009

(51) Int. Cl.
*A01H 1/00* (2006.01)
*A01H 5/00* (2006.01)
*A01H 5/10* (2006.01)
*C12N 15/82* (2006.01)

(52) U.S. Cl. .................. 800/312; 435/415; 800/260; 800/298; 800/300; 800/301; 800/302

(58) Field of Classification Search ............. None
See application file for complete search history.

(56) References Cited

U.S. PATENT DOCUMENTS

| | | | |
|---|---|---|---|
| 5,633,435 A * | 5/1997 | Barry et al. | 800/288 |
| 6,727,410 B1 * | 4/2004 | Steiger et al. | 800/312 |
| 6,855,875 B1 | 2/2005 | Stephens et al. | |
| 2006/0107364 A1 * | 5/2006 | Streit et al. | 800/312 |

OTHER PUBLICATIONS

Plant Variety Protection Act, Certificate No. 200100083 for SOYBEAN '93B87' issued Jun. 14, 2001.
Plant Variety Protection Act, Certificate No. 200400080 for SOYBEAN '93M11' issued Aug. 16, 2004.

* cited by examiner

*Primary Examiner*—David H Kruse
(74) *Attorney, Agent, or Firm*—Alston & Bird LLP

(57) ABSTRACT

According to the invention, there is provided a novel soybean variety designated XB39N09. This invention thus relates to the seeds of soybean variety XB39N09, to the plants of soybean XB39N09 to plant parts of soybean variety XB39N09 and to methods for producing a soybean plant produced by crossing plants of the soybean variety XB39N09 with another soybean plant, using XB39N09 as either the male or the female parent.

21 Claims, No Drawings

SOYBEAN VARIETY XB39N09

FIELD OF INVENTION

This invention relates generally the field of soybean breeding, specifically relating to a soybean variety designated XB39N09.

BACKGROUND OF INVENTION

The present invention relates to a new and distinctive soybean variety, designated XB39N09 which has been the result of years of careful breeding and selection as part of a soybean breeding program. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include but are not limited to higher seed yield, resistance to diseases and insects, tolerance to drought and heat, altered fatty acid profile, abiotic stress tolerance, improvements in compositional traits and better agronomic qualities.

These processes, which lead to the final step of marketing and distribution, can take from six to twelve years from the time the first cross is made. Therefore, development of new varieties is a time-consuming process that requires precise forward planning, efficient use of resources, and a minimum of changes in direction.

Soybean (*Glycine max*), is an important and valuable field crop. Thus, a continuing goal of soybean breeders is to develop stable, high yielding soybean varieties that are agronomically sound. The reasons for this goal are to maximize the amount of grain produced on the land used and to supply food for both animals and humans. To accomplish this goal, the soybean breeder must select and develop soybean plants that have the traits that result in superior varieties.

Pioneer soybean research staff create over 500,000 potential new varieties each year. Of those new varieties, less than 50 and more commonly less than 25 are actually selected for commercial use.

The soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board & American Soybean Association Special Report 92S, May 1990). Changes in fatty acid composition for improved oxidative stability and nutrition are also important traits. Industrial uses for processed soybean oil include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry, is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein.

For human consumption soybean meal is made into soybean flour which is processed to protein concentrates used for meat extenders or specialty pet foods. Production of edible protein ingredients from soybean offers a healthy, less expensive replacement for animal protein in meats as well as dairy-type products.

SUMMARY OF INVENTION

According to the invention, there is provided a novel soybean variety, designated XB39N09. This invention thus relates to the seeds of soybean variety XB39N09, to the plants of soybean XB39N09, to plant parts of soybean variety XB39N09 and to methods for producing a soybean plant produced by crossing soybean variety XB39N09 with another soybean plant, using XB39N09 as either the male or the female parent. This invention also relates to methods for introgressing a transgenic or mutant trait into soybean variety XB39N09 and to the soybean plants and plant parts produced by those methods. This invention also relates to soybean varieties or breeding varieties and plant parts derived from soybean variety XB39N09, to methods for producing other soybean varieties or plant parts derived from soybean variety XB39N09 and to the soybean plants, varieties, and their parts derived from use of those methods. This invention further relates to soybean seeds, plants, and plant parts produced by crossing the soybean variety XB39N09 with another soybean variety.

DEFINITIONS

Certain definitions used in the specification are provided below. Also in the examples which follow, a number of terms are used. In order to provide a clear and consistent understanding of the specification and claims, the following definitions are provided:

AERIAL WEB BLIGHT. Tolerance to Aerial Web Blight is rated on a scale of 1 to 9, with a score of 1 being very susceptible ranging up to a score of 9 being tolerant.

ALLELE. Any of one or more alternative forms of a genetic sequence. In a diploid cell or organism, the two alleles of a given sequence typically occupy corresponding loci on a pair of homologous chromosomes.

ALTER. The utilization of up-regulation, down-regulation, or gene silencing.

ANTHESIS. The time of a flower's opening.

APHID ANTIBIOSIS. Aphid antibiosis is the ability of a variety to reduce the survival, growth, or reproduction of aphids that feed on it. Screening scores are based on the ability of the plant to decrease the rate of aphid reproduction. Plants are compared to resistant and susceptible check plant grown in the same test. Scores of three=below average, 5=average, 7=above average and 9=exceptional.

BACKCROSSING. Process in which a breeder crosses a progeny variety back to one of the parental genotypes one or more times. Backcrossing can be used to introduce one or more locus conversions from one genetic background into another.

BREEDING. The genetic manipulation of living organisms. BU/A=Bushels per Acre. The seed yield in bushels/acre is the actual yield of the grain at harvest.

Brown Stem Rot=BSR=Brown Stem Rot Tolerance. This is a visual disease score from 1 to 9 comparing all genotypes in a given test. The score is based on leaf symptoms of yellowing and necrosis caused by brown stem rot. A score of 9 indicates no symptoms. Visual scores range down to a score of 1 which indicates severe symptoms of leaf yellowing and necrosis.

BSRLF=Brown Stem Rot disease rating based solely on leaf disease symptoms. This is a visual disease score from 1 to 9 comparing all genotypes in a given test. A score of 9 indicates no symptoms. Visual scores range down to a score of 1 which indicates severe symptoms.

BSRSTM=Brown Stem Rot disease rating based solely on stem disease symptoms. This is a visual disease score from 1 to 9 comparing all genotypes in a given test. A score of 9 indicates no symptoms. Visual scores range down to a score of 1 which indicates severe symptoms.

CELL. Cell as used herein includes a plant cell, whether isolated, in tissue culture or incorporated in a plant or plant part.

CHARCOAL ROT DISEASE. A fungal disease that is enhanced by hot and dry conditions, especially during reproductive growth stages. Score is based on observations of the comparative ability to tolerate drought and limit losses from charcoal rot infection among various soybean varieties.

CHLORIDE SENSITIVITY. This is a measure of the chloride concentration in the plant tissue from 1 to 9. The higher the score the lower the concentration of chloride concentration in the tissue measured.

CW or Canopy Width. This is visual observation of the canopy width from 1 to 9 comparing all genotypes in a given test. 9=extremely bushy and 1=very narrow.

CNKR or Stem Canker Tolerance. This is a visual disease score from 1 to 9 comparing all genotypes in a given field test. The score is based upon field reaction to the disease. A score of 9 indicates resistance to the disease, whereas a score of 1 indicates the line is susceptible to the disease.

STEM CANKER GENE. Resistance based on specific gene that infers specific resistance or susceptibility to a specific race of Stem Canker. Scores of nine=high degree of resistance, 5=provides moderate resistance, 1=no specific gene for resistance. This score is based upon a reaction of tooth pick inoculation. A score of 9 indicates no symptoms, whereas a score of 1 indicates experimental unit showed lesions relative to resistant and susceptible checks within the test.

COTYLEDON. A cotyledon is a type of seed leaf. The cotyledon contains the food storage tissues of the seed.

CROSS-POLLINATION. Fertilization by the union of two gametes from different plants.

DIPLOID. A cell or organism having two sets of chromosomes.

ELITE VARIETY. A variety that is sufficiently homozygous and homogeneous to be used for commercial grain production. An elite variety may also be used in further breeding.

EMBRYO. The embryo is the small plant contained within a mature seed.

EMGSC=Field Emergence=Emergence Score. A score based upon speed and strength of emergence at sub-optimal conditions. Rating occurs at unifoliate to first trifoliate. A score from 1 to 9 scale is given, with 9 being the best and 1 the poorest. 9, 8, 7—degrees of optimal stands; vigorous growth and plant health; 6, 5, 4—degrees of less than optimal stands; moderate growth and plant health; 3, 2, 1—degrees of unacceptable stands (potential replant situations); slow growth and poor plant health.

FEC=Iron-deficiency Chlorosis=Iron Chlorosis. Plants are scored 1 to 9 based on visual observations. A score of 1 indicates the plants are dead or dying from iron-deficiency chlorosis, a score of 5 means plants have intermediate health with some leaf yellowing and a score of 9 means no stunting of the plants or yellowing of the leaves. Plots are usually scored in mid July.

FECL=Iron-deficiency Chlorosis. Plants are scored 1 to 9 based on visual observations. A score of 1 indicates the plants are dead or dying from iron-deficiency chlorosis, a score of 5 means plants have intermediate health with some leaf yellowing and a score of 9 means no stunting of the plants or yellowing of the leaves. Plots are scored around mid August.

FEY or Frogeye Leaf Spot. This is a visual disease score from 1 to 9 comparing all genotypes in a given test. The score is based upon leaf lesions. A score of 9 indicates no lesions, whereas a score of 1 indicates severe leaf necrosis.

FLOWER COLOR. Data values include: P=purple and W=white.

GENE SILENCING. The interruption or suppression of the expression of a gene at the level of transcription or translation.

GENOTYPE. Refers to the genetic constitution of a cell or organism.

PLANT HABIT. This refers to the physical appearance of a plant. It can be determinate (Det), semi-determinate, intermediate, or indeterminate (Ind). In soybeans, indeterminate varieties are those in which stem growth is not limited by formation of a reproductive structure (i.e., flowers, pods and seeds) and hence growth continues throughout flowering and during part of pod filling. The main stem will develop and set pods over a prolonged period under favorable conditions. In soybeans, determinate varieties are those in which stem growth ceases at flowering time. Most flowers develop simultaneously, and most pods fill at approximately the same time. The terms semi-determinate and intermediate are also used to describe plant habit and are defined in Bernard, R. L. 1972. "Two genes affecting stem termination in soybeans." Crop Science 12:235-239; Woodworth, C. M. 1932. "Genetics and breeding in the improvement of the soybean." Bull. Agric. Exp. Stn. (Illinois) 384:297-404; Woodworth, C. M. 1933. "Genetics of the soybean." J. Am. Soc. Agron. 25:36-51.

HAPLOID. A cell or organism having one set of the two sets of chromosomes in a diploid.

HERBRES=Herbicide Resistance. This indicates that the plant is more tolerant to the herbicide shown than the level of herbicide tolerance exhibited by wild type plants. A designation of RR indicates tolerance to glyphosate and a designation of STS indicates tolerance to sulfonylurea herbicides.

HGT=Plant Height. Plant height is taken from the top of the soil to top pod of the plant and is measured in inches.

HILUM. This refers to the scar left on the seed which marks the place where the seed was attached to the pod prior to it (the seed) being harvested. Hila Color-data values include BR=brown; TN=tan; Y=yellow; BL=black IB=Imperfect Black; BF=buff.

HYPL=Hypocotyl length=Hypocotyl Elongation. This score indicates the ability of the seed to emerge when planted 3" deep in sand pots and with a controlled temperature of 25° C. The number of plants that emerge each day are counted. Based on this data, each genotype is given a 1 to 9 score based on its rate of emergence and percent of emergence. A score of 9 indicates an excellent rate and percent of emergence, an intermediate score of 5 indicates average ratings and a 1 score indicates a very poor rate and percent of emergence.

HYPOCOTYL. A hypocotyl is the portion of an embryo or seedling between the cotyledons and the root. Therefore, it can be considered a transition zone between shoot and root.

LDGSEV=Lodging Resistance=Harvest Standability. Lodging is rated on a scale of 1 to 9. A score of 9 indicates erect plants. A score of 5 indicates plants are leaning at a 45° angle in relation to the ground and a score of 1 indicates plants are laying on the ground.

LEAFLETS. These are part of the plant shoot, and they manufacture food for the plant by the process of photosynthesis.

LINKAGE. Refers to a phenomenon wherein alleles on the same chromosome tend to segregate together more often than expected by chance if their transmission was independent.

LINKAGE DISEQUILIBRIUM. Refers to a phenomenon wherein alleles tend to remain together in linkage groups when segregating from parents to offspring, with a greater frequency than expected from their individual frequencies.

LLC=Oil with three percent or less Linolenic acid is classified as low linolenic oil. Linolenic acid is one of the five most abundant fatty acids in soybean seeds. It is measured by gas chromatography and is reported as a percent of the total oil content.

LLE=Linoleic Acid Percent. Linoleic acid is one of the five most abundant fatty acids in soybean seeds. It is measured by gas chromatography and is reported as a percent of the total oil content.

LLN=Linolenic Acid Percent. Linolenic acid is one of the five most abundant fatty acids in soybean seeds. It is measured by gas chromatography and is reported as a percent of the total oil content.

LOCUS. A defined segment of DNA.

PRM Predicted Relative Maturity or Relative Maturity. Soybean maturities are divided into relative maturity groups (00, 0, I, II, III, IV . . . X or 00, 0, 1, 2, 3, . . . 10). Within maturity are sub-groups. A sub-group is a tenth of a relative maturity group (for example 1.3 would indicate a group 1 and subgroup 3).

MAT ABS=Absolute Maturity. This term is defined as the length of time from planting to complete physiological development (maturity). The period from planting until maturity is reached is measured in days, usually in comparison to one or more standard varieties. Plants are considered mature when 95% of the pods have reached their mature color.

MATURITY GROUP. This refers to an agreed-on industry division of groups of varieties, based on the zones in which they are adapted primarily according to day length or latitude. They consist of very long day length varieties (Groups 000, 00, 0), and extend to very short day length varieties (Groups VII, VIII, IX, X).

Narrow rows. Term indicates 7" and 15" row spacing.

NEI DISTANCE. A quantitative measure of percent similarity between two lines. Nei's distance between lines A and B can be defined as 1-(2*number alleles in common/(number alleles in A+number alleles in B). For example, if lines A and B are the same for 95 out of 100 alleles, the Nei distance would be 0.05. If lines A and B are the same for 98 out of 100 alleles, the Nei distance would be 0.02. Free software for calculating Nei distance is available on the internet at multiple locations such as, for example, at: evolution.genetics.washington.edu/phylip.html. See Nei, Proc Natl Acad Sci, 76:5269-5273 (1979) which is incorporated by reference for this purpose.

NUCLEIC ACID. An acidic, chainlike biological macromolecule consisting of multiple repeat units of phosphoric acid, sugar and purine and pyrimidine bases.

OIL=Oil Percent. Soybean seeds contain a considerable amount of oil. Oil is measured by NIR spectrophotometry, and is reported on an as is percentage basis.

Oil/Meal TYPE: Designates varieties specially developed with the following oil traits: HLC=High Oleic oil; LLC=Low Linolenic (3% linolenic content); ULC=Ultra Low Linolenic oil (1% linolenic oil content); HSC=High Sucrose meal; LPA=Low Phytic Acid; LST=Low Saturate oil; Blank=Conventional variety/oil composition.

OLC=Oleic Acid Percent. Oleic acid is one of the five most abundant fatty acids in soybean seeds. It is measured by gas chromatography and is reported as a percent of the total oil content.

PEDIGREE DISTANCE. Relationship among generations based on their ancestral links as evidenced in pedigrees. May be measured by the distance of the pedigree from a given starting point in the ancestry.

PERCENT IDENTITY. Percent identity as used herein refers to the comparison of the homozygous alleles of two soybean varieties. Percent identity is determined by comparing a statistically significant number of the homozygous alleles of two developed varieties. For example, a percent identity of 90% between soybean variety 1 and soybean variety 2 means that the two varieties have the same allele at 90% of their loci.

PERCENT SIMILARITY. Percent similarity as used herein refers to the comparison of the homozygous alleles of a soybean variety such as XB39N09 with another plant, and if the homozygous allele of XB39N09 matches at least one of the alleles from the other plant then they are scored as similar. Percent similarity is determined by comparing a statistically significant number of loci and recording the number of loci with similar alleles as a percentage. A percent similarity of 90% between XB39N09 and another plant means that XB39N09 matches at least one of the alleles of the other plant at 90% of the loci.

PLANT. As used herein, the term "plant" includes reference to an immature or mature whole plant, including a plant from which seed or grain or anthers have been removed. Seed or embryo that will produce the plant is also considered to be the plant.

PLANT PARTS. As used herein, the term "plant parts" includes leaves, stems, roots, root tips, anthers, seed, grain, embryo, pollen, ovules, flowers, cotyledon, hypocotyl, pod, flower, shoot and stalk, tissue, cells and the like.

PLM or Palmitic Acid Percent. Palmitic acid is one of the five most abundant fatty acids in soybean seeds. It is measured by gas chromatography and is reported as a percent of the total oil content.

PMG infested soils: soils containing *Phytophthora sojae*.

POD. This refers to the fruit of a soybean plant. It consists of the hull or shell (pericarp) and the soybean seeds. Pod Color data values include: BR=brown; TN=tan.

PRT or *Phytophthora* Field Tolerance. Tolerance to *Phytophthora* root rot is rated on a scale of 1 to 9, with a score of 9 being the best or highest tolerance ranging down to a score of 1 which indicates the plants have no tolerance to *Phytophthora*.

PHYTOPHTHORA RESISTANCE GENE. (–) no specific gene for resistance; 1a=resistance to races 1-2, 10-11, 13-8, 24; 1c=resistance to races 1-3, 6-11, 13, 15, 17, 21, 23, 24, 26, 28-30, 32, 34, 36. 1k=resistance to races 1-11, 13-15, 17, 18, 21-24, 26, 36, 37.; 6=resistance to races 1-4, 10, 12, 14-16, 18-21, 25, 28, 33-35.

PRMMAT or Predicted Relative Maturity. Soybean maturities are divided into relative maturity groups. In the United States the most common maturity groups are 00 through VIII. Within maturity groups 00 through V are sub-groups. A sub-group is a tenth of a relative maturity group. Within narrow comparisons, the difference of a tenth of a relative maturity group equates very roughly to a day difference in maturity at harvest.

PRO or Protein Percent. Soybean seeds contain a considerable amount of protein. Protein is generally measured by NIR spectrophotometry, and is reported on a dry weight basis.

PUBESCENCE. This refers to a covering of very fine hairs closely arranged on the leaves, stems and pods of the soybean plant. Pubescence Color-data values include: L=Light Tawny; T=Tawny; G=Gray.

R160 or Palmitic Acid percentage. Percentage of palmitic acid as determined using methods described in Reske, et al., Triacylglycerol Composition and Structure in Genetically Modified Sunflower and Soybean Oils. JAOCS 74:8, 989-998 (1997), which is incorporated by reference for this purpose.

R180 or Stearic acid percentage. Percentage of Stearic acid as determined using methods described in Reske, et al., Triacylglycerol Composition and Structure in Genetically Modified Sunflower and Soybean Oils. JAOCS 74:8, 989-998 (1997), which is incorporated by reference for this purpose.

R181 or Oleic acid percentage. Percentage of oleic acid as determined using methods described in Reske, et al., Triacylglycerol Composition and Structure in Genetically Modified Sunflower and Soybean Oils. JAOCS 74:8, 989-998 (1997), which is incorporated by reference for this purpose.

R182 or Linoleic acid percentage. Percentage of linoleic acid as determined using methods described in Reske, et al., Triacylglycerol Composition and Structure in Genetically Modified Sunflower and Soybean Oils. JAOCS 74:8, 989-998 (1997), which is incorporated by reference for this purpose.

R183 or Linolenic acid percentage. Percentage of linolenic acid as determined using methods described in Reske, et al., Triacylglycerol Composition and Structure in Genetically Modified Sunflower and Soybean Oils. JAOCS 74:8, 989-998 (1997), which is incorporated by reference for this purpose.

RESISTANCE. Synonymous with tolerance. The ability of a plant to withstand exposure to an insect, disease, herbicide or other condition. A resistant plant variety will have a level of resistance higher than a comparable wild-type variety.

RKI or Root-knot Nematode, Southern. This is a visual disease score from 1 to 9 comparing all genotypes in a given test. The score is based upon digging plants to visually score the roots for presence or absence of galling. A score of 9 indicates that there is no galling of the roots, a score of 1 indicates large severe galling cover most of the root system which results in pre-mature death from decomposing of the root system.

RKA or Root-knot Nematode, Peanut. This is a visual disease score from 1 to 9 comparing all genotypes in a given test. The score is based upon digging plants to look at the roots for presence or absence of galling. A score of 9 indicates that there is no galling of the roots, a score of 1 indicates large severe galling cover most of the root system which results in pre-mature death from decomposing of the root system.

SCN=Soybean Cyst Nematode Resistance=Cyst Nematode Resistance. The score is based on resistance to a particular race of soybean cyst nematode, such as race 1, 2, 3, 5 or 14. Scores are visual observations of resistance as versus other genotypes in the test, with a higher score indicating a higher level of resistance.

SCN Resistance Source. There are three sources of genetic resistance to SCN: P188788, P1548402 (also known as Peking), and P1437654 (also known as Hartwig).

SCN infected soils: soils containing soybean cyst nematode.

SD VIG or Seedling Vigor. The score is based on the speed of emergence of the plants within a plot relative to other plots within an experiment. A score of 9 indicates that 90% of plants growing have expanded first leaves. A score of 1 indicates no plants have expanded first leaves.

SDS or Sudden Death Syndrome. Tolerance to Sudden Death Syndrome is rated on a scale of 1 to 9, with a score of 1 being very susceptible ranging up to a score of 9 being tolerant.

SEED COAT LUSTER. Data values include D=dull; S=shiny.

SEED SIZE SCORE. This is a measure of the seed size from 1 to 9. The higher the score the smaller the seed size measured.

SPLB=S/LB=Seeds per Pound. Soybean seeds vary in seed size, therefore, the number of seeds required to make up one pound also varies. This affects the pounds of seed required to plant a given area, and can also impact end uses.

SHATTR or Shattering. This refers to the amount of pod dehiscence prior to harvest. Pod dehiscence involves seeds falling from the pods to the soil. This is a visual score from 1 to 9 comparing all genotypes within a given test. A score of 9 means pods have not opened and no seeds have fallen out and a score of 1 indicates 100% of the pods are opened.

SHOOTS. These are a portion of the body of the plant. They consist of stems, petioles and leaves.

STC or Stearic Acid Percent. Stearic acid is one of the five most abundant fatty acids in soybean seeds. It is measured by gas chromatography and is reported as a percent of the total oil content.

SUBLINE. Although XB39N09 contains substantially fixed genetics, and is phenotypically uniform and with no off-types expected, there still remains a small proportion of segregating loci either within individuals or within the population as a whole. A breeder of ordinary skill in the art may fix these loci by making them more uniform in order to optimize the performance of the variety. One example of this type of approach is described in the "breeding bias" methods described in U.S. Pat. No. 5,437,697 and U.S. patent application Ser. No. 10/901,425 may be utilized by a breeder of ordinary skill in the art to further purify the variety in order to increase its yield. By sublining in this manner, no crosses to a different variety are made, and so a new genetic variety is not created and the overall genetic composition of the variety remains essentially the same.

WH MD or White Mold Tolerance. This is a visual disease score from 1 to 9 comparing all genotypes in a given test. The score is based upon observations of mycelial growth and death of plants. A score of 9 indicates no symptoms. Visual scores of 1 indicate complete death of the experimental unit.

VARIETY. A substantially homozygous soybean line and minor modifications thereof that retain the overall genetics of the soybean line including but not limited to a subline, a locus conversion, a mutation, a transgene, or a somaclonal variant.

High yield environments. Areas which lack normal stress for example they have sufficient rainfall, water drainage, low disease pressure, and low weed pressure Tough environments. Areas which have stress challenges, opposite of a high yield environment

DETAILED DESCRIPTION OF INVENTION

The variety of the invention has shown uniformity and stability for all traits, as described in the following variety description information. It has been self-pollinated a sufficient number of generations, with careful attention to uniformity of plant type to ensure a sufficient level of homozygosity and phenotypic stability. The variety has been increased with continued observation for uniformity. No variant traits have been observed or are expected.

Strengths of Soybean variety XB39N09 include glyphosate resistance, multi-race *Phytophthora* resistance (Rps1k), moderate iron deficiency chlorosis tolerance, moderate sudden death syndrome field tolerance, strong emergence, and excellent harvest standability.

Soybean variety XB39N09 demonstrates a valuable combination of traits. There are few other varieties at this RM which have the yield potential, multi-race *phytophthora* resistance as governed by the Rps1-k gene, and glyphosate resistance that XB39N09 has.

Soybean variety XB39N09 exhibits a relative maturity of 3 and a subgroup of approximately 9. A variety description of Soybean variety XB39N09 is provided in Table 1. Traits reported are average values for all locations and years or samples measured.

Soybean variety XB39N09, being substantially homozygous, can be reproduced by planting seeds of the variety, growing the resulting soybean plants under self-pollinating or sib-pollinating conditions, and harvesting the resulting seed, using techniques familiar to the agricultural arts.

Performance Examples of XB39N09

In the examples in Table 2, the traits and characteristics of soybean variety XB39N09 are given in paired comparisons with the Pioneer varieties shown in the following tables. Traits reported are mean values for all locations and years where paired comparison data was obtained.

FURTHER EMBODIMENTS OF THE INVENTION

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et. al, "An Integrated Genetic Linkage Map of the Soybean Genome" Crop Science 39:1464-1490 (1999), and Berry et al., Assessing Probability of Ancestry Using Simple Sequence Repeat Profiles: Applications to Maize Inbred Lines and Soybean Varieties" Genetics 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for XB39N09. For example, one set of publicly available markers which could be used to screen and identify variety XB39N09 is disclosed in Table 3.

Primers and PCR protocols for assaying these and other markers are disclosed in the Soybase (sponsored by the USDA Agricultural Research Service and Iowa State University) located at the world wide web at 129.186.26.94/SSR.html. In addition to being used for identification of soybean variety XB39N09 and plant parts and plant cells of variety XB39N09, the genetic profile may be used to identify a soybean plant produced through the use of XB39N09 or to verify a pedigree for progeny plants produced through the use of XB39N09. The genetic marker profile is also useful in breeding and developing backcross conversions.

The present invention comprises a soybean plant characterized by molecular and physiological data obtained from the representative sample of said variety deposited with the ATCC. Further provided by the invention is a soybean plant formed by the combination of the disclosed soybean plant or plant cell with another soybean plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Primers used are publicly available and may be found in the Soybase or Cregan supra. See also, PCT Publication No. WO 99/31964 Nucleotide Polymorphisms in Soybean, U.S. Pat. No. 6,162,967 Positional Cloning of Soybean Cyst Nematode Resistance Genes, and US2002/0129402A1 Soybean Sudden Death Syndrome Resistant Soybeans and Methods of Breeding and Identifying Resistant Plants, the disclosure of which are incorporated herein by reference.

The SSR profile of soybean plant XB39N09 can be used to identify plants comprising XB39N09 as a parent, since such plants will comprise the same homozygous alleles as XB39N09. Because the soybean variety is essentially homozygous at all relevant loci, most loci should have only one type of allele present. In contrast, a genetic marker profile of an F1 progeny should be the sum of those parents, e.g., if one parent was homozygous for allele x at a particular locus, and the other parent homozygous for allele y at that locus, then the F1 progeny will be xy (heterozygous) at that locus. Subsequent generations of progeny produced by selection and breeding are expected to be of genotype x (homozygous), y (homozygous), or xy (heterozygous) for that locus position. When the F1 plant is selfed or sibbed for successive filial generations, the locus should be either x or y for that position.

In addition, plants and plant parts substantially benefiting from the use of XB39N09 in their development, such as XB39N09 comprising a backcross conversion, transgene, or genetic sterility factor, may be identified by having a molecular marker profile with a high percent identity to XB39N09. Such a percent identity might be 95%, 96%, 97%, 98%, 99%, 99.5% or 99.9% identical to XB39N09.

The SSR profile of XB39N09 also can be used to identify essentially derived varieties and other progeny varieties developed from the use of XB39N09, as well as cells and other plant parts thereof. Such plants may be developed using the markers identified in WO 00/31964, U.S. Pat. No. 6,162,967 and US2002/0129402A1. Progeny plants and plant parts produced using XB39N09 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from soybean variety, as measured by either percent identity or percent similarity. Such progeny may be further characterized as being within a pedigree distance of XB39N09, such as within 1,2,3,4 or 5 or less cross-pollinations to a soybean plant other than XB39N09, or a plant that has XB39N09 as a progenitor. Unique molecular profiles may be identified with other molecular tools such as SNPs and RFLPs.

Introduction of a New Trait or Locus into XB39N09

Variety XB39N09 represents a new base genetic variety into which a new locus or trait may be introgressed. Direct transformation and backcrossing represent two important methods that can be used to accomplish such an introgression.

Backcross Conversions of XB39N09

A backcross conversion of XB39N09 occurs when DNA sequences are introduced through backcrossing (Hallauer et al, 1988), with XB39N09 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: Proceedings Symposium of the Analysis of Molecular Data, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Hallauer et al. in Corn and Corn Improvement, Sprague and Dudley, Third Ed. 1998). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal or viral), insect resistance and herbicide resistance. In addition, an introgression site itself, such as an FRT site, Lox site or other site specific integration site, may be inserted by backcrossing and utilized for direct insertion of one or more genes of interest into a specific plant variety. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, Breeding Field Crops, P. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant and easily recognized traits.

One process for adding or modifying a trait or locus in soybean variety XB39N09 comprises crossing XB39N09 plants grown from XB39N09 seed with plants of another soybean variety that comprise the desired trait or locus, selecting F1 progeny plants that comprise the desired trait or locus to produce selected F1 progeny plants, crossing the selected progeny plants with the XB39N09 plants to produce backcross progeny plants, selecting for backcross progeny plants that have the desired trait or locus and the morphological characteristics of soybean variety XB39N09 to produce selected backcross progeny plants; and backcrossing to XB39N09 three or more times in succession to produce selected fourth or higher backcross progeny plants that comprise said trait or locus. The modified XB39N09 may be further characterized as having the physiological and morphological characteristics of soybean variety XB39N09 listed in Table 1 as determined at the 5% significance level when grown in the same environmental conditions and/or may be characterized by percent similarity or identity to XB39N09 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox and other sites for site specific integration, which may also affect a desired trait if a functional nucleic acid is inserted at the integration site.

In addition, the above process and other similar processes described herein may be used to produce first generation progeny soybean seed by adding a step at the end of the process that comprises crossing XB39N09 with the introgressed trait or locus with a different soybean plant and harvesting the resultant first generation progeny soybean seed.

Transgenes

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are inserted into the genome using transformation, backcrossing or other methods known to one of skill in the art are referred to herein collectively as "transgenes". Over the last fifteen to twenty years several methods for producing transgenic plants have been developed, and the present invention also relates to transgenic variants of the claimed soybean variety XB39N09.

One embodiment of the invention is a process for producing soybean variety XB39N09, further comprising a desired trait, said process comprising transforming a soybean plant of variety XB39N09 with a transgene that confers a desired trait. Another embodiment is the product produced by this process. In one embodiment the desired trait may be one or more of herbicide resistance, insect resistance, disease resistance, decreased phytate, or modified fatty acid or carbohydrate metabolism. The specific gene may be any known in the art or listed herein, including: a polynucleotide conferring resistance to imidazolinone, sulfonylurea, glyphosate, glufosinate, triazine and benzonitrile; a polynucleotide encoding a *bacillus thuringiensis* polypeptide, a polynucleotide encoding phytase, FAD-2, FAD-3, galactinol synthase or a raffinose synthetic enzyme; or a polynucleotide conferring resistance to soybean cyst nematode, brown stem rot, *phytophthora* root rot, soybean mosaic virus or sudden death syndrome.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into the genome of a particular soybean plant may then be moved into the genome of another variety using traditional breeding techniques that are well known in the plant breeding arts. For example, a backcrossing approach is commonly used to move a transgene from a transformed soybean variety into an already developed soybean variety, and the resulting backcross conversion plant would then comprise the transgene(s).

Various genetic elements can be introduced into the plant genome using transformation. These elements include, but are not limited to genes; coding sequences; inducible, constitutive, and tissue specific promoters; enhancing sequences; and signal and targeting sequences. For example, see the traits, genes and transformation methods listed in U.S. Pat. No. 6,118,055.

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

A genetic map can be generated, primarily via conventional Restriction Fragment Length Polymorphisms (RFLP), Polymerase Chain Reaction (PCR) analysis, Simple Sequence Repeats (SSR) and Single Nucleotide Polymorphisms (SNP) that identifies the approximate chromosomal location of the integrated DNA molecule. For exemplary methodologies in this regard, see Glick and Thompson, METHODS IN PLANT MOLECULAR BIOLOGY AND BIOTECHNOLOGY 269-284 (CRC Press, Boca Raton, 1993).

Wang et al. discuss "Large Scale Identification, Mapping and Genotyping of Single-Nucleotide Polymorphisms in the Human Genome", Science, 280:1077-1082, 1998, and similar capabilities are becoming increasingly available for the soybean genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Likewise, by means of the present invention, plants can be genetically engineered to express various phenotypes of agronomic interest. Through the transformation of soybean the expression of genes can be altered to enhance disease resistance, insect resistance, herbicide resistance, agronomic, grain quality and other traits. Transformation can also be used to insert DNA sequences which control or help control malesterility. DNA sequences native to soybean as well as non-native DNA sequences can be transformed into soybean and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, *The Maize Handbook* ch. 118 (Springer-Verlag 1994) or other genetic elements such as a FRT, Lox or other site specific integration site, antisense technology (see, e.g., Sheehy et al. (1988) *PNAS* USA 85:8805-8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340-344; Flavell (1994) *PNAS USA* 91:3490-3496; Finnegan et al. (1994) *Bio/Technology* 12:883-888; and Neuhuber et al. (1994) *Mol. Gen. Genet.* 244:230-241); RNA interference (Napoli et al. (1990) *Plant Cell* 2:279-289; U.S. Pat. No. 5,034,323; Sharp (1999) *Genes*

Dev. 13:139-141; Zamore et al. (2000) *Cell* 101:25-33; and Montgomery et al. (1998) *PNAS USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) *Plant Cell* 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Exemplary nucleotide sequences that may be altered by genetic engineering include, but are not limited to, those categorized below.

1. Transgenes That Confer Resistance To Insects or Disease And That Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis RSP2* gene for resistance to *Pseudomonas syringae*), McDowell & Woffenden, (2003) Trends Biotechnol. 21(4):178-83 and Toyoda et al., (2002) Transgenic Res. 11(6):567-82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 7,105,332; 7,208,474; WO 91/14778; WO 99/31248; WO 01/12731; WO 99/24581; WO 97/40162 and U.S. application Ser. Nos. 10/032,717; 10/414,637; 11/018,615; 11/404,297; 11/404,638; 11/471,878; 11/780,501; 11/780,511; 11/780,503; 11/953,648; 11/953,648; and 11/957,893.

(C) An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

(D) An insect-specific peptide which, upon expression, disrupts the physiology of the affected pest. For example, see the disclosures of Regan, *J. Biol. Chem.* 269:9 (1994) (expression cloning yields DNA coding for insect diuretic hormone receptor); Pratt et al., *Biochem. Biophys. Res. Comm.* 163:1243 (1989) (an allostatin is identified in *Diploptera puntata*); Chattopadhyay et al. (2004) Critical Reviews in Microbiology 30(1): 33-54 2004; Zjawiony (2004) J Nat Prod 67(2): 300-310; Carlini & Grossi-de-Sa (2002) Toxicon, 40(11): 1515-1539; Ussuf et al. (2001) Curr Sci. 80(7): 847-853; and Vasconcelos & Oliveira (2004) Toxicon 44(4):385-403. See also U.S. Pat. No. 5,266,317 to Tomalski et al., who disclose genes encoding insect-specific toxins.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT Application No. WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene, and U.S. Pat. Nos. 6,563,020; 7,145,060 and 7,087,810.

(G) A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

(H) A hydrophobic moment peptide. See PCT Application No. WO 95/16776 and U.S. Pat. No. 5,580,852 disclosure of peptide derivatives of Tachyplesin which inhibit fungal plant pathogens) and PCT Application No. WO 95/18855 and U.S. Pat. No. 5,607,914 (teaches synthetic antimicrobial peptides that confer disease resistance).

(I) A membrane permease, a channel former or a channel blocker. For example, see the disclosure by Jaynes et al., *Plant Sci.* 89: 43 (1993), of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki et al., *Nature* 366:469 (1993), who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2:367 (1992).

(N) A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5(2) (1995), Pieterse & Van Loon (2004) Curr. Opin. Plant Bio. 7(4):456-64 and Somssich (2003) Cell 113(7):815-6.

(P) Antifungal genes (Cornelissen and Melchers, Pl. Physiol. 101:709-712, (1993) and Parijs et al., Planta 183: 258-264, (1991) and Bushnell et al., Can. J. of Plant Path. 20(2):137-149 (1998). Also see U.S. application Ser. Nos. 09/950,933; 11/619,645; 11/657,710; 11/748,994; 11/774,121 and U.S. Pat. Nos. 6,891,085 and 7,306,946.

(Q) Detoxification genes, such as for fumonisin, beauvericin, moniliformin and zearalenone and their structurally related derivatives. For example, see U.S. Pat. Nos. 5,716,820; 5,792,931; 5,798,255; 5,846,812; 6,083,736; 6,538,177; 6,388,171 and 6,812,380.

(R) Cystatin and cysteine proteinase inhibitors. See U.S. Pat. No. 7,205,453.

(S) Defensin genes. See WO 03/000863 and U.S. Pat. Nos. 6,911,577; 6,855,865; 6,777,592 and 7,238,781.

(T) Genes conferring resistance to nematodes. See e.g. PCT Application WO 96/30517; PCT Application No. WO 93/19181, WO 03/033651 and Urwin et al., Planta 204:472-479 (1998), Williamson (1999) Curr Opin Plant Bio. 2(4): 327-31; and U.S. Pat. Nos. 6,284,948 and 7,301,069.

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al, *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

2. Transgenes That Confer Resistance To A Herbicide, For Example:

(A) A herbicide that inhibits the growing point or meristem, such as an imidazolinone or a sulfonylurea. Exemplary genes in this category code for mutant ALS and AHAS enzyme as described, for example, by Lee et al., EMBO J. 7: 1241 (1988), and Miki et al., *Theor. Appl. Genet.* 80:449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; U.S. application Ser. No. 11/683,737, and PCT Publication No. WO 96/33270.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. Nos. 10/427, 692; 10/835,615 and 11/507,751. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Patent No. 0 242 246 and 0 242 236 to Leemans et al. De Greef et al., *Bio/Technology* 7: 61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose. Exemplary genes conferring resistance to phenoxy proprionic acids and cyclohexones, such as sethoxydim and haloxyfop, are the Acc1-S1, Acc1-S2 and Acc1-S3 genes described by Marshall et al., *Theor. Appl. Genet.* 83:435 (1992).

(C) A herbicide that inhibits photosynthesis, such as a triazine (psbA and gs+ genes) and a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

(D) Acetohydroxy acid synthase, which has been found to make plants that express this enzyme resistant to multiple types of herbicides, has been introduced into a variety of plants (see, e.g., Hattori et al. (1995) Mol Gen Genet. 246: 419). Other genes that confer resistance to herbicides include: a gene encoding a chimeric protein of rat cytochrome P4507A1 and yeast NADPH-cytochrome P450 oxidoreductase (Shiota et al. (1994) Plant Physiol 106:17), genes for glutathione reductase and superoxide dismutase (Aono et al. (1995) Plant Cell Physiol 36:1687, and genes for various phosphotransferases (Datta et al. (1992) Plant Mol Biol 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and PCT Publication No. WO 01/12825.

3. Transgenes That Confer Or Contribute To an Altered Grain Characteristic, Such As:
  (A) Altered fatty acids, for example, by
    (1) Down-regulation of stearoyl-ACP desaturase to increase stearic acid content of the plant. See Knultzon et al., *Proc. Natl. Acad. Sci. USA* 89:2624 (1992) and WO 99/64579 (Genes for Desaturases to Alter Lipid Profiles in Corn),
    (2) Elevating oleic acid via FAD-2 gene modification and/or decreasing linolenic acid via FAD-3 gene modification (see U.S. Pat. Nos. 6,063,947; 6,323,392; 6,372,965 and WO 93/11245),
    (3) Altering conjugated linolenic or linoleic acid content, such as in WO 01/12800,
    (4) Altering LEC1, AGP, Dek1, Superal1, mi1ps, various Ipa genes such as Ipa1, Ipa3, hpt or hggt. For example, see WO 02/42424, WO 98/22604, WO 03/011015, U.S. Pat. No. 6,423,886, U.S. Pat. No. 6,197,561, U.S. Pat. No. 6,825,397, US2003/0079247, US2003/0204870, WO 02/057439, WO 03/011015 and Rivera-Madrid, R. et al. Proc. Natl. Acad. Sci. 92:5620-5624 (1995).
  B) Altered phosphorus content, for example, by the
    (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.
    (2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 05/113778 and/or by altering inositol kinase activity as in WO 02/059324, US2003/0009011, WO 03/027243, US2003/0079247, WO 99/05298, U.S. Pat. No. 6,197,561, U.S. Pat. No. 6,291,224, U.S. Pat. No. 6,391,348, WO 02/059324, US2003/0079247, WO 98/45448, WO 99/55882, WO 01/04147.
  (C) Altered carbohydrates effected, for example, by altering a gene for an enzyme that affects the branching pattern of starch or, a gene altering thioredoxin such as NTR and/or TRX (see. (See U.S. Pat. No. 6,531,648 which is incorporated by reference for this purpose) and/or a gamma zein knock out or mutant such as cs27 or TUSC27 or en27 (See U.S. Pat. No. 6,858,778 and US2005/0160488, US2005/0204418; which are incorporated by reference for this purpose). See Shiroza et al., J. Bacteriol. 170:810 (1988) (nucleotide sequence of *Streptococcus mutans* fructosyltransferase gene), Steinmetz et al., Mol. Gen. Genet. 200:220 (1985) (nucleotide sequence of *Bacillus subtilis* levansucrase gene), Pen et al., Bio/Technology 10:292 (1992) (production of transgenic plants that express *Bacillus licheniformis* alpha-amylase), Elliot et al., Plant Molec. Biol. 21:515 (1993) (nucleotide sequences of tomato invertase genes), Søgaard et al., J. Biol. Chem. 268: 22480 (1993) (site-directed mutagenesis of barley alpha-amylase gene), and Fisher et al., Plant Physiol. 102:1045 (1993) (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGF)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels, and WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 99/40209 (alteration of amino acid compositions in seeds), WO 99/29882 (methods for altering amino acid content of proteins), U.S. Pat. No. 5,850,016 (alteration of amino acid compositions in seeds), WO 98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 98/56935 (plant amino acid biosynthetic enzymes), WO 98/45458 (engineered seed protein having higher percentage of essential amino acids), WO 98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 96/01905 (increased threonine), WO 95/15392 (increased lysine), US2003/0163838, US2003/0150014, US2004/0068767, U.S. Pat. No. 6,803,498, WO 01/79516.

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the barnase and the barstar gene (Paul et al. Plant Mol. Biol. 19:611-622, 1992).

For additional examples of nuclear male and female sterility systems and genes, see also, U.S. Pat. Nos. 5,859,341; 6,297,426; 5,478,369; 5,824,524; 5,850,014; and 6,265,640; all of which are hereby incorporated by reference.

5. Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821, which are hereby incorporated by reference. Other systems that may be used include the Gin recombinase of phage Mu (Maeser et al., 1991; Vicki Chandler, *The Maize Handbook ch.* 118 (Springer-Verlag 1994), the Pin recombinase of *E. coli* (Enomoto et al., 1983), and the R/RS system of the pSRi plasmid (Araki et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 00/060089, WO 01/026459, WO 00/1035725, WO 01/034726, WO 01/035727, WO 00/1036444, WO 01/036597, WO 01/036598, WO 00/2015675, WO 02/017430, WO 02/077185, WO 02/079403, WO 03/013227, WO 03/013228, WO 03/014327, WO 04/031349, WO 04/076638, WO 98/09521, and WO 99/38977 describing genes, including CBF genes and transcription factors effective in mitigating the negative effects of freezing, high salinity, and drought on plants, as well as conferring other positive effects on plant phenotype; US2004/0148654 and WO 01/36596 where abscisic acid is altered in plants resulting in improved plant phenotype such as increased yield and/or increased tolerance to abiotic stress; WO 00/006341, WO 04/090143, U.S. application Ser. Nos. 10/817,483 and 09/545,334 where cytokinin expression is modified resulting in plants with increased stress tolerance, such as drought tolerance, and/or increased yield. Also see WO 02/02776, WO 03/052063, JP2002281975, U.S. Pat. No. 6,084,153, WO 01/64898, U.S. Pat. No. 6,177,275, and U.S. Pat. No. 6,107,547 (enhancement of nitrogen utilization and altered nitrogen responsiveness). For ethylene alteration, see US2004/0128719, US2003/0166197 and WO 00/32761. For plant transcription factors or transcriptional regulators of abiotic stress, see e.g. US2004/0098764 or US2004/0078852.

Other genes and transcription factors that affect plant growth and agronomic traits such as yield, flowering, plant growth and/or plant structure, can be introduced or introgressed into plants, see e.g. WO 97/49811 (LHY), WO 98/56918 (ESD4), WO 97/10339 and U.S. Pat. No. 6,573,430 (TFL), U.S. Pat. No. 6,713,663 (FT), WO 96/14414 (CON), WO 96/38560, WO 01/21822 (VRN1), WO 00/44918 (VRN2), WO 99/49064 (GI), WO 00/46358 (FRI), WO 97/29123, U.S. Pat. No. 6,794,560, U.S. Pat. No. 6,307,126 (GAI), WO 99/09174 (D8 and Rht), and WO 04/076638 and WO 04/031349 (transcription factors).

Plant Breeding Techniques

Development of Soybean Sublines

Sublines of XB39N09 may also be developed. Although XB39N09 contains substantially fixed genetics, and is phenotypically uniform and with no off-types expected, there still remains a small proportion of segregating loci either within individuals or within the population as a whole. Sublining provides the ability to select for these loci, which have no apparent morphological or phenotypic effect on the plant characteristics, but do have an affect on overall yield. For example, the "breeding bias" methods described in U.S. Pat. No. 5,437,697 and U.S. patent application Ser. No. 10/901,425 may be utilized by a breeder of ordinary skill in the art to identify genetic loci that are associated with yield potential to further purify the variety in order to increase its yield. U.S. Pat. No. 5,437,697 and U.S. patent application Ser. No. 10/901,425 are incorporated by reference for this purpose. Based on these teachings, a breeder of ordinary skill in the art may fix agronomically important loci by making them homozygous in order to optimize the performance of the variety. No crosses to a different variety are made, and so a new genetic variety is not created and the overall genetic composition of the variety remains essentially the same. The development of soybean sublines and the use of accelerated yield technology is a plant breeding technique.

Using XB39N09 to Develop Other Soybean Varieties

Soybean varieties such as XB39N09 are typically developed for use in seed and grain production. However, soybean varieties such as XB39N09 also provide a source of breeding material that may be used to develop new soybean varieties. Plant breeding techniques known in the art and used in a soybean plant breeding program include, but are not limited to, recurrent selection, mass selection, bulk selection, backcrossing, pedigree breeding, open pollination breeding, restriction fragment length polymorphism enhanced selection, genetic marker enhanced selection, making double haploids, and transformation. Often combinations of these techniques are used. The development of soybean varieties in a plant breeding program requires, in general, the development and evaluation of homozygous varieties. There are many analytical methods available to evaluate a new variety. The oldest and most traditional method of analysis is the observation of phenotypic traits but genotypic analysis may also be used.

Using XB39N09 in a Breeding Program

This invention is directed to methods for producing a soybean plant by crossing a first parent soybean plant with a second parent soybean plant wherein the first and/or second parent soybean plant is variety XB39N09. The other parent may be any soybean plant, such as a soybean plant that is part of a synthetic or natural population. Any such methods using soybean variety XB39N09 are part of this invention: selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can be found in one of several reference books (e.g., Allard, *Principles of Plant Breeding*, 1960; Simmonds, *Principles of Crop Improvement*, 1979; Sneep et al., 1979; Fehr, "Breeding Methods for Cultivar Development", Chapter 7, *Soybean Improvement, Production and Uses*, $2^{nd}$ ed., Wilcox editor, 1987).

Pedigree Breeding

Pedigree breeding starts with the crossing of two genotypes, such as XB39N09 and another soybean variety having one or more desirable characteristics that is lacking or which complements XB39N09. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: F1→F2; F2→F3; F3→F4; F4→F$_5$, etc. After a sufficient amount of inbreeding, successive filial generations will serve to increase seed of the developed variety. Preferably, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a soybean variety may be crossed with another variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet several of the desired attributes of the non-recurrent parent. This approach leverages the value and strengths of the recurrent parent for use in new soybean varieties.

Therefore, an embodiment of this invention is a method of making a backcross conversion of soybean variety XB39N09, comprising the steps of crossing a plant of soybean variety XB39N09 with a donor plant comprising a desired trait, selecting an F1 progeny plant comprising the desired trait, and backcrossing the selected F1 progeny plant to a plant of soybean variety XB39N09. This method may further comprise the step of obtaining a molecular marker profile of soybean variety XB39N09 and using the molecular marker profile to select for a progeny plant with the desired trait and the molecular marker profile of XB39N09. In one embodiment the desired trait is a mutant gene or transgene present in the donor parent.

Recurrent Selection and Mass Selection

Recurrent selection is a method used in a plant breeding program to improve a population of plants. XB39N09 is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation Breeding

Mutation breeding is another method of introducing new traits into soybean variety XB39N09. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in "Principles of Cultivar Development" Fehr, 1993 Macmillan Publishing Company. In addition, mutations created in other soybean plants may be used to produce a backcross conversion of XB39N09 that comprises such mutation.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing XB39N09.

Isozyme Electrophoresis and RFLPs have been widely used to determine genetic composition. Shoemaker and Olsen, ((1993) Molecular Linkage Map of Soybean (*Glycine max* L. Merr.). p. 6.131-6.138. In S. J. O'Brien (ed.) Genetic Maps: Locus Maps of Complex Genomes. Cold Spring Harbor Laboratory Press. Cold Spring Harbor, N.Y.), developed a molecular genetic linkage map that consisted of 25 linkage groups with about 365 RFLP, 11 RAPD (random amplified polymorphic DNA), three classical markers, and four isozyme loci. See also, Shoemaker R. C. 1994 RFLP Map of Soybean. P. 299-309 In R. L. Phillips and I. K. Vasil (ed.) DNA-based markers in plants. Kluwer Academic Press Dordrecht, the Netherlands.

SSR technology is an efficient and practical marker technology; more marker loci can be routinely used and more alleles per marker locus can be found using SSRs in comparison to RFLPs. For example Diwan and Cregan, described a highly polymorphic microsatellite loci in soybean with as many as 26 alleles. (Diwan, N., and P. B. Cregan 1997 Automated sizing of fluorescent-labeled simple sequence repeat (SSR) markers to assay genetic variation in Soybean Theor. Appl. Genet. 95:220-225). Single Nucleotide Polymorphisms (SNPs) may also be used to identify the unique genetic composition of the invention and progeny varieties retaining that unique genetic composition. Various molecular marker techniques may be used in combination to enhance overall resolution.

Soybean DNA molecular marker linkage maps have been rapidly constructed and widely implemented in genetic studies. One such study is described in Cregan et. al, "An Integrated Genetic Linkage Map of the Soybean Genome" Crop Science 39:1464-1490 (1999). Sequences and PCR conditions of SSR Loci in Soybean as well as the most current genetic map may be found in Soybase on the world wide web.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection.

Production of Double Haploids

The production of double haploids can also be used for the development of plants with a homozygous phenotype in the breeding program. For example, a soybean plant for which XB39N09 is a parent can be used to produce double haploid plants. Double haploids are produced by the doubling of a set of chromosomes (1N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77:889-892, 1989 and US2003/0005479. This can be advantageous because the process omits the generations of selfing needed to obtain a homozygous plant from a heterozygous source.

Methods for obtaining haploid plants are disclosed in Kobayashi, M. et al., Journ. of Heredity 71(1):9-14, 1980, Pollacsek, M., Agronomie (Paris) 12(3):247-251, 1992; Cho-Un-Haing et al., Journ. of Plant Biol., 1996, 39(3):185-188; Verdoodt, L., et al., February 1998, 96(2):294-300; Genetic Manipulation in Plant Breeding, Proceedings International Symposium Organized by EUCARPIA, Sep. 8-13, 1985, Berlin, Germany; Chalyk et al., 1994, Maize Genet Coop. Newsletter 68:47; Chalyk, S.

Thus, an embodiment of this invention is a process for making a substantially homozygous XB39N09 progeny plant by producing or obtaining a seed from the cross of XB39N09 and another soybean plant and applying double haploid methods to the F1 seed or F1 plant or to any successive filial generation. Based on studies in maize and currently being conducted in soybean, such methods would decrease the number of generations required to produce a variety with similar genetics or characteristics to XB39N09. See Bernardo, R. and Kahler, A. L., Theor. Appl. Genet. 102:986-992, 2001.

In particular, a process of making seed retaining the molecular marker profile of soybean variety XB39N09 is contemplated, such process comprising obtaining or producing F1 seed for which soybean variety XB39N09 is a parent, inducing doubled haploids to create progeny without the occurrence of meiotic segregation, obtaining the molecular marker profile of soybean variety XB39N09, and selecting progeny that retain the molecular marker profile of XB39N09.

Use Of XB39N09 In Tissue Culture

This invention is also directed to the use of variety XB39N09 in tissue culture. Tissue culture of various tissues of soybeans and regeneration of plants therefrom is well known and widely published. For example, reference may be had to Komatsuda, T. et al., "Genotype X Sucrose Interactions for Somatic Embryogenesis in Soybean," Crop Sci. 31:333-337 (1991); Stephens, P. A. et al., "Agronomic Evaluation of Tissue-Culture-Derived Soybean Plants," Theor. Appl. Genet. (1991) 82:633-635; Komatsuda, T. et al., "Maturation and Germination of Somatic Embryos as Affected by Sucrose and Plant Growth Regulators in Soybeans Glycine gracilis Skvortz and Glycine max (L.) Merr.," Plant Cell, Tissue and Organ Culture, 28:103-113 (1992); Dhir, S. et al., "Regeneration of Fertile Plants from Protoplasts of Soybean (Glycine max L. Merr.): Genotypic Differences in Culture Response," Plant Cell Reports (1992) 11:285-289; Pandey, P. et al., "Plant Regeneration from Leaf and Hypocotyl Explants of Glycine wightii (W. and A.) VERDC. var. longicauda," Japan J. Breed. 42:1-5 (1992); and Shetty, K., et al., "Stimulation of In Vitro Shoot Organogenesis in Glycine max (Merrill.) by Allantoin and Amides," Plant Science 81:(1992) 245-251; as well as U.S. Pat. No. 5,024,944, issued Jun. 18, 1991 to Collins et al. and U.S. Pat. No. 5,008,200, issued Apr. 16, 1991 to Ranch et al., the disclosures of which are hereby incorporated herein in their entirety by reference. Thus, another aspect of this invention is to provide cells which upon growth and differentiation produce soybean plants having the physiological and morphological characteristics of soybean variety XB39N09.

REFERENCES

Aukerman, M. J. et al. (2003) "Regulation of Flowering Time and Floral Organ Identity by a MicroRNA and Its APETALA2-like Target Genes" The Plant Cell 15:2730-2741

Berry et al., Assessing Probability of Ancestry Using Simple Sequence Repeat Profiles: Applications to Maize Inbred Lines and Soybean Varieties" Genetics 165:331-342 (2003)

Boppenmaier, et al., "Comparisons Among Strains of Inbreds for RFLPs", Maize Genetics Cooperative Newsletter, 65:1991, p. 90

Conger, B. V., et al. (1987) "Somatic Embryogenesis From Cultured Leaf Segments of Zea Mays", Plant Cell Reports, 6:345-347

Cregan et al, "An Integrated Genetic Linkage Map of the Soybean Genome" Crop Science 39:1464-1490 (1999).

Diwan et al., "Automated sizing of fluorescent-labeled simple sequence repeat (SSR) markers to assay genetic variation in Soybean" Theor. Appl. Genet. 95:220-225. (1997).

Duncan, D. R., et al. (1985) "The Production of Callus Capable of Plant Regeneration From Immature Embryos of Numerous Zea Mays Genotypes", Planta, 165:322-332

Edallo, et al. (1981) "Chromosomal Variation and Frequency of Spontaneous Mutation Associated with in Vitro Culture and Plant Regeneration in Maize", Maydica, XXVI:39-56

Fehr, Walt, Principles of Cultivar Development, pp. 261-286 (1987)
Green, et al. (1975) "Plant Regeneration From Tissue Cultures of Maize", *Crop Science, Vol.* 15, pp. 417-421
Green, C. E., et al. (1982) "Plant Regeneration in Tissue Cultures of Maize" *Maize for Biological Research*, pp. 367-372
Hallauer, A. R. et al. (1988) "Corn Breeding" *Corn and Corn Improvement*, No. 18, pp. 463-481
Lee, Michael (1994) "Inbred Lines of Maize and Their Molecular Markers", *The Maize Handbook*, Ch. 65:423-432
Meghji, M. R., et al. (1984) "Inbreeding Depression, Inbred & Hybrid Grain Yields, and Other Traits of Maize Genotypes Representing Three Eras", *Crop Science, Vol.* 24, pp. 545-549
Openshaw, S. J., et al. (1994) "Marker-assisted selection in backcross breeding". pp. 41-43. In Proceedings of the Symposium Analysis of Molecular Marker Data. 5-7 Aug. 1994. Corvallis, Oreg., American Society for Horticultural Science/Crop Science Society of America
Phillips, et al. (1988) "Cell/Tissue Culture and In Vitro Manipulation", *Corn & Corn Improvement*, 3rd Ed., ASA Publication, No. 18, pp. 345-387
Poehlman et al (1995) *Breeding Field Crop*, 4th Ed., Iowa State University Press, Ames, Iowa., pp. 132-155 and 321-344
Rao, K. V., et al., (1986) "Somatic Embryogenesis in Glume Callus Cultures", *Maize Genetics Cooperative Newsletter*, No. 60, pp. 64-65
Sass, John F. (1977) "Morphology", *Corn & Corn Improvement*, ASA Publication, Madison, Wis. pp. 89-109
Smith, J. S. C., et al., "The Identification of Female Selfs in Hybrid Maize: A Comparison Using Electrophoresis and Morphology", Seed Science and Technology 14, 1-8
Songstad, D. D. et al. (1988) "Effect of ACC(1-aminocyclo-propane-1-carboyclic acid), Silver Nitrate & Norbonadiene on Plant Regeneration From Maize Callus Cultures", *Plant Cell Reports*, 7:262-265
Tomes, et al. (1985) "The Effect of Parental Genotype on Initiation of Embryogenic Callus From Elite Maize (*Zea Mays* L.) Germplasm", *Theor. Appl. Genet.*, Vol. 70, p. 505-509
Troyer, et al. (1985) "Selection for Early Flowering in Corn: 10 Late Synthetics", *Crop Science*, Vol. 25, pp. 695-697
Umbeck, et al. (1983) "Reversion of Male-Sterile T-Cytoplasm Maize to Male Fertility in Tissue Culture", *Crop Science*, Vol. 23, pp. 584-588
Wan et al., "Efficient Production of Doubled Haploid Plants Through Colchicine Treatment of Anther-Derived Maize Callus", Theoretical and Applied Genetics, 77:889-892, 1989
Wright, Harold (1980) "Commercial Hybrid Seed Production", *Hybridization of Crop Plants*, Ch. 8:161-176
Wych, Robert D. (1988) "Production of Hybrid Seed", *Corn and Corn Improvement*, Ch. 9, pp. 565-607

DEPOSITS

Applicant made a deposit of seeds of Soybean Variety XB39N09 with the American Type Culture Collection (ATCC), Manassas, Va. 20110 USA, ATCC Deposit No. PTA-11286. The seeds deposited with the ATCC on Sep. 8, 2010 were taken from the seed stock maintained by Pioneer Hi-Bred International, Inc., 7250 NW 62$^{nd}$ Avenue, Johnston, Iowa 50131 since prior to the filing date of this application. Access to this seed stock will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. This deposit of Soybean Variety XB39N09 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 C.F.R. §§1.801-1.809, including providing an indication of the viability of the sample upon deposit. Applicant has no authority to waive any restrictions imposed by law on the transfer of biological material or its transportation in commerce. Applicant does not waive any infringement of their rights granted under this patent or under the Plant Variety Protection Act (7 USC 2321 et seq.).

TABLE 1

Variety Description Information for XB39N09

| Current Variety Name | XB39N09 |
|---|---|
| Relative Maturity | 3.9 |
| Herbicide Resistance | Glyphosate Resistance |
| Yield Potential | |
| Harvest Standability | 8 |
| Field Emergence | 7 |
| Hypocotyl Length | 9 |
| Phytophthora Gene | 1K |
| Phytophthora Race 5 | |
| Phytophthora Race 7 | |
| Phytophthora Race 25 | |
| Phytophthora Field Tolerance | 4 |
| Brown Stem Rot | |
| Iron Chlorosis | 5 |
| White Mold Tolerance | |
| Sudden Death Syndrome | 5 |
| Cyst Nematode Race 1 | |
| Cyst Nematode Race 2 | |
| Cyst Nematode Race 3 | |
| Cyst Nematode Race 5 | |
| Cyst Nematode Race 14 | |
| Aphid Antibiosis | 5 |
| Root-knot Nematode-Southern | |
| Root-knot Nematode-Peanut | |
| Stem Canker Genetic | |
| Stem Canker Tolerance | |
| Frogeye Leaf Spot | |
| Aerial Web Blight | |
| Chloride Sensitivity | |
| Canopy Width | |
| Shattering | |
| Plant Habit | Ind |
| Oil/Meal Type | |
| Seed Protein (% @13% H20) | |
| Seed Oil (% @13% H20) | |
| Seed Size Score | 6 |
| Seed Size Range (avg seeds/lb) | |
| Flower Color | W |
| Pubescence Color | L |
| Hila Color | BL |
| Pod Color | TN |
| Seed Coat Luster | |

TABLE 2

VARIETY COMPARISON DATA

| Variety1 | Variety2 | Statistic | YIELD bu/a 60# ABS | MATABS count ABS | HGT in ABS | LDGSEV score ABS |
|---|---|---|---|---|---|---|
| XB39N09 | 93M70 | Mean1 | 53.7 | 133.9 | 37.1 | 8 |
| XB39N09 | 93M70 | Mean2 | 51.3 | 131.1 | 37.3 | 5 |

TABLE 2-continued

VARIETY COMPARISON DATA

| XB39N09 | 93M70 | #Locs | 51 | 20 | 12 | 15 |
|---|---|---|---|---|---|---|
| XB39N09 | 93M70 | #Reps | 95 | 34 | 21 | 23 |
| XB39N09 | 93M70 | #Years | 3 | 3 | 2 | 2 |
| XB39N09 | 93M70 | % Wins | 72.5 | 95 | 66.7 | 100 |
| XB39N09 | 93M70 | Diff | 2.4 | 2.8 | 0.2 | 3 |
| XB39N09 | 93M70 | SE Diff | 0.75 | 0.43 | 0.83 | 0.4 |
| XB39N09 | 93M70 | Prob | 0.0023 | 0 | 0.8312 | 0 |
| XB39N09 | 93M92 | Mean1 | 53.7 | 133.9 | 37.1 | 8 |
| XB39N09 | 93M92 | Mean2 | 50.7 | 133.6 | 37.5 | 6 |
| XB39N09 | 93M92 | #Locs | 51 | 20 | 12 | 15 |
| XB39N09 | 93M92 | #Reps | 93 | 34 | 21 | 23 |
| XB39N09 | 93M92 | #Years | 3 | 3 | 2 | 2 |
| XB39N09 | 93M92 | % Wins | 68.6 | 60 | 58.3 | 80 |
| XB39N09 | 93M92 | Diff | 3 | 0.3 | 0.4 | 2 |
| XB39N09 | 93M92 | SE Diff | 0.91 | 0.41 | 0.92 | 0.4 |
| XB39N09 | 93M92 | Prob | 0.0018 | 0.4101 | 0.6481 | 0.0012 |
| XB39N09 | 93Y71 | Mean1 | 51.1 | 134.8 | 34.7 | 8 |
| XB39N09 | 93Y71 | Mean2 | 51.5 | 130.2 | 37.6 | 6 |
| XB39N09 | 93Y71 | #Locs | 29 | 10 | 8 | 9 |
| XB39N09 | 93Y71 | #Reps | 63 | 21 | 16 | 15 |
| XB39N09 | 93Y71 | #Years | 1 | 1 | 1 | 1 |
| XB39N09 | 93Y71 | % Wins | 44.8 | 100 | 87.5 | 100 |
| XB39N09 | 93Y71 | Diff | −0.3 | 4.6 | 2.8 | 2 |
| XB39N09 | 93Y71 | SE Diff | 0.66 | 0.63 | 1.01 | 0.3 |
| XB39N09 | 93Y71 | Prob | 0.6318 | 0 | 0.0267 | 0.0006 |
| XB39N09 | 93Y80 | Mean1 | 51.1 | 134.8 | 34.7 | 8 |
| XB39N09 | 93Y80 | Mean2 | 50.4 | 132.5 | 34.1 | 8 |
| XB39N09 | 93Y80 | #Locs | 29 | 10 | 8 | 9 |
| XB39N09 | 93Y80 | #Reps | 62 | 21 | 16 | 15 |
| XB39N09 | 93Y80 | #Years | 1 | 1 | 1 | 1 |
| XB39N09 | 93Y80 | % Wins | 65.5 | 100 | 50 | 44 |
| XB39N09 | 93Y80 | Diff | 0.8 | 2.3 | −0.7 | 0 |
| XB39N09 | 93Y80 | SE Diff | 0.89 | 0.34 | 0.79 | 0.4 |
| XB39N09 | 93Y80 | Prob | 0.3897 | 0.0001 | 0.4252 | 0.808 |
| XB39N09 | 93Y90 | Mean1 | 53.3 | 134 | 37.1 | 8 |
| XB39N09 | 93Y90 | Mean2 | 51.7 | 134.1 | 41.6 | 7 |
| XB39N09 | 93Y90 | #Locs | 49 | 19 | 12 | 15 |
| XB39N09 | 93Y90 | #Reps | 92 | 33 | 21 | 23 |
| XB39N09 | 93Y90 | #Years | 2 | 2 | 2 | 2 |
| XB39N09 | 93Y90 | % Wins | 63.3 | 42.1 | 91.7 | 67 |
| XB39N09 | 93Y90 | Diff | 1.6 | −0.1 | 4.4 | 1 |
| XB39N09 | 93Y90 | SE Diff | 0.89 | 0.44 | 0.6 | 0.2 |
| XB39N09 | 93Y90 | Prob | 0.0855 | 0.767 | 0 | 0.0018 |

| Variety1 | Variety2 | Statistic | SPLB count ABS | SDS score ABS | PROTN pct ABS | OILPCT pct ABS |
|---|---|---|---|---|---|---|
| XB39N09 | 93M70 | Mean1 | 3015 | 6.8 | 33.59 | 19.84 |
| XB39N09 | 93M70 | Mean2 | 3048 | 7.5 | 34.3 | 19.81 |
| XB39N09 | 93M70 | #Locs | 8 | 6 | 7 | 7 |
| XB39N09 | 93M70 | #Reps | 8 | 15 | 8 | 8 |
| XB39N09 | 93M70 | #Years | 3 | 1 | 2 | 2 |
| XB39N09 | 93M70 | % Wins | 63 | 16.7 | 28.57 | 57.14 |
| XB39N09 | 93M70 | Diff | −33 | −0.7 | −0.71 | 0.02 |
| XB39N09 | 93M70 | SE Diff | 80.2 | 0.38 | 0.257 | 0.127 |
| XB39N09 | 93M70 | Prob | 0.6922 | 0.1261 | 0.0334 | 0.8677 |
| XB39N09 | 93M92 | Mean1 | 3015 | 6.8 | 33.59 | 19.84 |
| XB39N09 | 93M92 | Mean2 | 3076 | 6.8 | 34.3 | 19.09 |
| XB39N09 | 93M92 | #Locs | 8 | 6 | 7 | 7 |
| XB39N09 | 93M92 | #Reps | 8 | 15 | 8 | 8 |
| XB39N09 | 93M92 | #Years | 3 | 1 | 2 | 2 |
| XB39N09 | 93M92 | % Wins | 38 | 16.7 | 14.29 | 100 |
| XB39N09 | 93M92 | Diff | −61 | 0 | −0.71 | 0.75 |
| XB39N09 | 93M92 | SE Diff | 80.4 | 0.35 | 0.262 | 0.117 |
| XB39N09 | 93M92 | Prob | 0.4749 | 0.9399 | 0.0346 | 0.0007 |
| XB39N09 | 93Y71 | Mean1 | 2871 | 6.8 | 32.91 | 19.54 |
| XB39N09 | 93Y71 | Mean2 | 3160 | 7.3 | 32.6 | 18.83 |
| XB39N09 | 93Y71 | #Locs | 4 | 6 | 4 | 4 |
| XB39N09 | 93Y71 | #Reps | 4 | 15 | 5 | 5 |
| XB39N09 | 93Y71 | #Years | 1 | 1 | 1 | 1 |
| XB39N09 | 93Y71 | % Wins | 0 | 16.7 | 75 | 100 |
| XB39N09 | 93Y71 | Diff | −289 | −0.5 | 0.31 | 0.71 |
| XB39N09 | 93Y71 | SE Diff | 49.2 | 0.47 | 0.514 | 0.17 |
| XB39N09 | 93Y71 | Prob | 0.0098 | 0.3614 | 0.5876 | 0.0245 |
| XB39N09 | 93Y80 | Mean1 | 2871 | 6.8 | 32.91 | 19.54 |
| XB39N09 | 93Y80 | Mean2 | 3373 | 7.7 | 31.29 | 19 |
| XB39N09 | 93Y80 | #Locs | 4 | 6 | 4 | 4 |
| XB39N09 | 93Y80 | #Reps | 4 | 15 | 5 | 5 |
| XB39N09 | 93Y80 | #Years | 1 | 1 | 1 | 1 |
| XB39N09 | 93Y80 | % Wins | 0 | 0 | 100 | 100 |
| XB39N09 | 93Y80 | Diff | −502 | −0.9 | 1.63 | 0.54 |
| XB39N09 | 93Y80 | SE Diff | 148.9 | 0.29 | 0.126 | 0.131 |
| XB39N09 | 93Y80 | Prob | 0.0433 | 0.0324 | 0.001 | 0.026 |
| XB39N09 | 93Y90 | Mean1 | 3019 | 6.8 | 33.59 | 19.84 |
| XB39N09 | 93Y90 | Mean2 | 3093 | 7.6 | 34.06 | 17.99 |
| XB39N09 | 93Y90 | #Locs | 7 | 6 | 7 | 7 |
| XB39N09 | 93Y90 | #Reps | 7 | 15 | 8 | 8 |
| XB39N09 | 93Y90 | #Years | 2 | 1 | 2 | 2 |
| XB39N09 | 93Y90 | % Wins | 14 | 0 | 14.29 | 100 |
| XB39N09 | 93Y90 | Diff | −74 | −0.8 | −0.47 | 1.85 |
| XB39N09 | 93Y90 | SE Diff | 65.7 | 0.28 | 0.303 | 0.168 |
| XB39N09 | 93Y90 | Prob | 0.3026 | 0.0463 | 0.1707 | 0 |

TABLE 3

Soybean SSR Marker Set

| | | | |
|---|---|---|---|
| SAC1006 | SATT129 | SATT243 | SATT334 |
| SAC1611 | SATT130 | SATT247 | SATT335 |
| SAC1634 | SATT131 | SATT249 | SATT336 |
| SAC1677 | SATT133 | SATT250 | SATT338 |
| SAC1699 | SATT142 | SATT251 | SATT339 |
| SAC1701 | SATT144 | SATT255 | SATT343 |
| SAC1724 | SATT146 | SATT256 | SATT346 |
| SAT_084 | SATT147 | SATT257 | SATT347 |
| SAT_090 | SATT150 | SATT258 | SATT348 |
| SAT_104 | SATT151 | SATT259 | SATT352 |
| SAT_117 | SATT153 | SATT262 | SATT353 |
| SAT_142-DB | SATT155 | SATT263 | SATT355 |
| SAT_189 | SATT156 | SATT264 | SATT356 |
| SAT_222-DB | SATT165 | SATT265 | SATT357 |
| SAT_261 | SATT166 | SATT266 | SATT358 |
| SAT_270 | SATT168 | SATT267 | SATT359 |
| SAT_271-DB | SATT172 | SATT270 | SATT361 |
| SAT_273-DB | SATT175 | SATT272 | SATT364 |
| SAT_275-DB | SATT181 | SATT274 | SATT367 |
| SAT_299 | SATT183 | SATT279 | SATT369 |
| SAT_301 | SATT186 | SATT280 | SATT373 |
| SAT_311-DB | SATT190 | SATT282 | SATT378 |
| SAT_317 | SATT191 | SATT284 | SATT380 |
| SAT_319-DB | SATT193 | SATT285 | SATT383 |
| SAT_330-DB | SATT195 | SATT287 | SATT385 |
| SAT_331-DB | SATT196 | SATT292 | SATT387 |
| SAT_343 | SATT197 | SATT295 | SATT389 |
| SAT_351 | SATT199 | SATT299 | SATT390 |
| SAT_366 | SATT202 | SATT300 | SATT391 |
| SAT_381 | SATT203 | SATT307 | SATT393 |
| SATT040 | SATT204 | SATT314 | SATT398 |
| SATT042 | SATT212 | SATT319 | SATT399 |
| SATT050 | SATT213 | SATT321 | SATT406 |
| SATT092 | SATT216 | SATT322 | SATT409 |
| SATT102 | SATT219 | SATT326 | SATT411 |
| SATT108 | SATT221 | SATT327 | SATT412 |
| SATT109 | SATT225 | SATT328 | SATT413 |
| SATT111 | SATT227 | SATT330 | SATT414 |
| SATT115 | SATT228 | SATT331 | SATT415 |
| SATT122 | SATT230 | SATT332 | SATT417 |
| SATT127 | SATT233 | SATT333 | SATT418 |
| SATT420 | SATT508 | SATT583 | SATT701 |
| SATT421 | SATT509 | SATT584 | SATT708-TB |
| SATT422 | SATT510 | SATT586 | SATT712 |
| SATT423 | SATT511 | SATT587 | SATT234 |
| SATT429 | SATT512 | SATT590 | SATT240 |
| SATT431 | SATT513 | SATT591 | SATT242 |
| SATT432 | SATT514 | SATT594 | |
| SATT433 | SATT515 | SATT595 | |
| SATT436 | SATT517 | SATT596 | |
| SATT440 | SATT519 | SATT597 | |
| SATT441 | SATT522 | SATT598 | |
| SATT442 | SATT523 | SATT601 | |

TABLE 3-continued

Soybean SSR Marker Set

| | | |
|---|---|---|
| SATT444 | SATT524 | SATT602 |
| SATT448 | SATT526 | SATT608 |
| SATT451 | SATT529 | SATT613 |
| SATT452 | SATT533 | SATT614 |
| SATT454 | SATT534 | SATT617 |
| SATT455 | SATT536 | SATT618 |
| SATT457 | SATT537 | SATT628 |
| SATT460 | SATT540 | SATT629 |
| SATT461 | SATT544 | SATT630 |
| SATT464 | SATT545 | SATT631 |
| SATT466 | SATT546 | SATT632-TB |
| SATT467 | SATT548 | SATT633 |
| SATT469 | SATT549 | SATT634 |
| SATT470 | SATT550 | SATT636 |
| SATT471 | SATT551 | SATT640-TB |
| SATT473 | SATT552 | SATT651 |
| SATT475 | SATT555 | SATT654 |
| SATT476 | SATT556 | SATT655-TB |
| SATT477 | SATT557 | SATT656 |
| SATT478 | SATT558 | SATT660 |
| SATT479 | SATT565 | SATT661-TB |
| SATT480 | SATT566 | SATT662 |
| SATT487 | SATT567 | SATT665 |
| SATT488 | SATT568 | SATT666 |
| SATT491 | SATT569 | SATT667 |
| SATT492 | SATT570 | SATT672 |
| SATT493 | SATT572 | SATT675 |
| SATT495 | SATT573 | SATT677 |
| SATT497 | SATT576 | SATT678 |
| SATT503 | SATT578 | SATT680 |
| SATT506 | SATT581 | SATT684 |
| SATT507 | SATT582 | SATT685 |

All publications, patents and patent applications mentioned in the specification are indicative of the level of those skilled in the art to which this invention pertains. All such publications, patents and patent applications are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

What is claimed:

1. Soybean variety XB39N09, representative seed of said soybean variety XB39N09 having been deposited under ATCC Accession Number PTA-11286.

2. A seed of the soybean variety of claim 1.

3. A soybean plant obtained by transforming the soybean variety of claim 1 with a transgene.

4. The soybean plant of claim 3, wherein the transgene confers a trait selected from the group consisting of male sterility, site-specific recombination, abiotic stress tolerance, altered phosphorus, altered antioxidants, altered fatty acids, altered essential amino acids, altered carbohydrates, herbicide resistance, insect resistance and disease resistance.

5. A soybean plant, or a part thereof, produced by growing the seed of claim 2.

6. A tissue culture produced from protoplasts or regenerable cells from the plant of claim 5.

7. A method for developing a second soybean plant in a soybean plant breeding program comprising applying plant breeding techniques to a first soybean plant, or parts thereof, wherein said first soybean plant is the soybean plant of claim 5, and wherein application of said techniques results in development of said second soybean plant.

8. A method for producing soybean seed comprising crossing two soybean plants and harvesting the resultant soybean seed, wherein at least one soybean plant is the soybean plant of claim 5.

9. The soybean seed produced by the method of claim 8.

10. A soybean plant, or part thereof, produced by growing said seed of claim 9.

11. A method for developing a second soybean plant in a soybean plant breeding program comprising applying plant breeding techniques to a first soybean plant, or parts thereof, wherein said first soybean plant is the soybean plant of claim 10, and wherein application of said techniques results in development of said second soybean plant.

12. A method of producing a soybean plant comprising a locus conversion, the method comprising introducing a locus conversion into the plant of claim 5, wherein said locus conversion is selected from the group consisting of male sterility, site-specific recombination, abiotic stress tolerance, altered phosphorus, altered antioxidants, altered fatty acids, altered essential amino acids, altered carbohydrates, herbicide resistance, insect resistance and disease resistance.

13. A herbicide resistant soybean plant produced by the method of claim 12.

14. A disease resistant soybean plant produced by the method of claim 12.

15. An insect resistant soybean plant produced by the method of claim 12.

16. The soybean plant of claim 15, wherein the transgene encodes a *Bacillus thuringiensis* (Bt) endotoxin.

17. A soybean plant obtained by transforming the plant of claim 5, with a transgene.

18. The plant of claim 17, wherein the transgene confers a trait selected from the group consisting of male sterility, site-specific recombination, abiotic stress tolerance, altered phosphorus, altered antioxidants, altered fatty acids, altered essential amino acids, altered carbohydrates, herbicide resistance, insect resistance and disease resistance.

19. A method for developing a second soybean plant in a soybean plant breeding program comprising applying plant breeding techniques to a first soybean plant, or parts thereof, wherein said first soybean plant is the soybean plant of claim 17, and wherein application of said techniques results in development of said second soybean plant.

20. A soybean plant, or a part thereof, expressing all the physiological and morphological characteristics of soybean variety XB39N09, representative seed of said soybean variety XB39N09 having been deposited under ATCC Accession Number PTA-11286.

21. A seed of the soybean plant of claim 3.

\* \* \* \* \*